United States Patent
Bristow

(10) Patent No.: US 9,936,696 B2
(45) Date of Patent: Apr. 10, 2018

(54) AGROCHEMICAL COMPOSITIONS FOR REDUCING AGROCHEMICAL RESIDUES

(71) Applicant: ROTAM AGROCHEM INTERNATIONAL COMPANY LIMITED, Chai Wan (HK)

(72) Inventor: James Timothy Bristow, Chai Wan (HK)

(73) Assignee: ROTAM AGROCHEM INTERNATIONAL COMPANY LIMITED, Chai Wan (HK)

( * ) Notice: Subject to any disclaimer, the term of this patent is extended or adjusted under 35 U.S.C. 154(b) by 0 days.

(21) Appl. No.: 14/397,227

(22) PCT Filed: Apr. 26, 2013

(86) PCT No.: PCT/CN2013/074758
§ 371 (c)(1),
(2) Date: Oct. 27, 2014

(87) PCT Pub. No.: WO2013/159731
PCT Pub. Date: Oct. 31, 2013

(65) Prior Publication Data
US 2015/0126370 A1 May 7, 2015

(30) Foreign Application Priority Data

Apr. 27, 2012 (CN) .......................... 2012 1 0130353

(51) Int. Cl.
*A01N 37/40* (2006.01)
*A01N 25/12* (2006.01)

(52) U.S. Cl.
CPC ............. *A01N 37/40* (2013.01); *A01N 25/12* (2013.01)

(58) Field of Classification Search
None
See application file for complete search history.

(56) References Cited

U.S. PATENT DOCUMENTS

| 8,252,721 B2 | 8/2012 | Bettarini et al. |
| 2006/0122060 A1* | 6/2006 | Keenan ................ A01N 25/12 504/211 |
| 2010/0016160 A1 | 1/2010 | Bettarini et al. |

FOREIGN PATENT DOCUMENTS

| CN | 1390456 | 1/2003 |
| CN | 1433688 | 6/2003 |
| CN | 1681391 A | 10/2005 |
| CN | 1010578046 | 11/2009 |
| CN | 102365967 | 1/2011 |
| EP | 1917857 | 5/2008 |
| WO | 2004/023876 A1 | 3/2004 |
| WO | 2008071377 | 6/2008 |
| WO | 2012048176 A2 | 4/2012 |
| ZA | 2002/06143 | 1/2002 |

OTHER PUBLICATIONS

International Search Report for PCT/CN2013/074758 dated Jul. 25, 2013.
French Search Report on Application FR1353778 dated Apr. 25, 2013.
Search Report and Written Opinion, dated Nov. 3, 2014, issued in corresponding French Patent Application No. 1353778.
Search Report, dated Jul. 15, 2015, issued in corresponding European Patent Application No. 13 780 670.9.
Search Report, dated Oct. 2, 2013, issued in corresponding Great Britain Application No. 1307548.6.
Search Report, dated Sep. 7, 2015, issued in corresponding Chinese Patent Application (Application/Patent Nos. 201210130353.4; 2015090105214460).

* cited by examiner

Primary Examiner — Alton N Pryor
(74) Attorney, Agent, or Firm — Dickinson Wright PLLC

(57) ABSTRACT

An agrochemical composition containing dicamba or its salt, a sulfonamide herbicide free acid and a solid base. A method of controlling field weeds with the use of the composition. A method of reducing and/or removing agrochemical composition residues in an application tank, as well as a method of preparing an agrochemical composition, including the mixing of a solid base with dicamba or its salt and a sulfonamide herbicide free acid.

12 Claims, No Drawings

AGROCHEMICAL COMPOSITIONS FOR REDUCING AGROCHEMICAL RESIDUES

This application is a 371 national phase entry of PCT/CN2013/074758, filed 26 Apr. 2013, which claims benefit of CN 201210130353.4, filed 27 Apr. 2012, the entire contents of which are incorporated herein by reference for all purposes.

BACKGROUND

Technical Field

The present disclosure relates to an agrochemical composition comprising dicamba or its salt, a sulfonamide herbicide free acid and a solid base. The present disclosure also relates to a method of controlling field weeds with the use of the said composition. Furthermore, the present disclosure relates to a method of reducing and/or removing agrochemical composition residues in an application tank, as well as a method of preparing an agrochemical composition, comprising the mixing of a solid base with dicamba or its salt and a sulfonamide herbicide free acid.

Description of Related Art

Sulfonamide herbicides are a class of compounds of high herbicidal activity with sulfonylurea or triazolopyrimidine as core structure. Compared with other conventional herbicides, sulfonamide herbicides show significantly higher herbicidal activity. However, the cost of sulfonamide herbicides is relatively high. In addition, the effect of sulfonamide herbicides on controlling monocotyledonous weeds is better than that on dicotyledonous weeds. Therefore, agrochemical compositions comprising the combined use of a sulfonamide herbicide and other herbicides are known in the art.

The combined use of a sulfonamide herbicide and dicamba or its salt exhibits significant synergism with better controlling effect on monocotyledonous and dicotyledonous weeds. It broadens the herbicidal spectrum, lowers the cost and shortens the farming time. Moreover, application in multiple amount of normal field usage is not only safe to the growing crops, but also safe to the succeeding crops thereafter. CN1169441 discloses an herbicidal formulation for controlling weeds in corn fields, which comprises a mixture of dicamba or its salt and nicosulfuron. The examples disclose a wettable powder of 1% dicamba+6% nicosulfuron; an aqueous suspension of 5% dicamba+1% nicosulfuron; an emulsion concentrate of 9% dicamba+1% nicosulfuron; and an aqueous solution of 39% dicamba+1% nicosulfuron. CN1433688 discloses an herbicidal formulation for controlling weeds, which comprises a mixture of dicamba or its salt and tribenuron-methyl. The examples disclose a wettable powder of 40% dicamba+4% tribenuron-methyl; a dry flowable of 48% dicamba+2% tribenuron-methyl; and a wettable powder of 49% dicamba+1% tribenuron-methyl. CN102365967 discloses an herbicidal composition for wheat fields, which comprises mesosulfuron-methyl and dicamba. The examples disclose a wettable powder of 19.5% dicamba+1% mesosulfuron-methyl; a wettable powder of 29.2% dicamba+1.5% mesosulfuron-methyl; a wettable powder of 39.2% dicamba+1.8% mesosulfuron-methyl; a water-dispersible granule of 34.3% dicamba+1.5% mesosulfuron-methyl; a suspension of 58.3% dicamba+3% mesosulfuron-methyl; and an emulsion concentrate of 50.8% dicamba+1.8% mesosulfuron-methyl. Sulfonamide herbicides are a class of highly active pesticides. Therefore, it is necessary to remove all sulfonamide residues carefully from the spray equipment (spray tank) used for applying pesticides on crops before using it to treat crops sensitive to sulfonamide or that would be damaged by sulfonamide used in the previous application. Adequate cleanout may require a rinsing procedure that is time-consuming and results in wastewater disposal problem. In the examples of CN1169441, the herbicidal mixtures of dicamba and nicosulfuron, formulated as emulsion concentrates, aqueous solutions, aqueous suspensions and wettable powders, have an amount of 1%-6% nicosulfuron. In the examples of CN1433688, the herbicidal mixtures of dicamba and tribenuron-methyl, formulated as wettable powders and dry flowables, have an amount of 1%-4% tribenuron-methyl. In the examples of CN102365967, the herbicidal mixtures of dicamba and mesosulfuron-methyl, formulated as wettable powders, water-dispersible granules, suspensions and emulsion concentrates, have an amount of 1%-3% mesosulfuron-methyl. In the abovementioned herbicidal mixtures of dicamba and sulfonamide, the amount of sulfonamides is relatively low, ranging from 1% to 6%. Since the amount of sulfonamides is low, there may not be any residue remaining in the spray tank or the amount of residue remaining is limited. However, a further increase in the amount of sulfonamides in the mixture of dicamba and sulfonamides inevitably results in sulfonamide residues remaining in the spray tank. Large quantity of water is required to wash the spray tank in order to reduce the amount of insoluble contaminative sulfonamide residues.

SUMMARY

In view of the above shortcomings, the present invention, in an embodiment, provides an agrochemical composition for controlling field weeds, which comprises dicamba or its salt, a sulfonamide herbicide free acid and a solid base. The agrochemical composition according to the present invention can be in solid form, for example, in the form of wettable powder or water-soluble granule, preferably in the form of water-soluble granule (SG).

In the first aspect, the present invention provides an agrochemical composition for controlling field weeds, which comprises dicamba or its salt, a sulfonamide herbicide free acid and a solid base, and optionally any agriculturally acceptable carriers. At least one of the following ingredients may be added to the said agrochemical composition as required: wetting agents, dispersing agents and diluents.

In an embodiment, the said agrochemical composition is in solid form. Preferably, the said agrochemical composition is in the form of wettable powder (WP), water-soluble powder (SP) or water-soluble granule (SG), more preferably in the form of water-soluble granule.

Under normal conditions, the agrochemical composition according to the present invention is ultimately applied in liquid form (e.g. solution, emulsion, or suspension). Therefore, the present invention also includes these liquid agrochemical compositions.

In another embodiment, the said solid base is selected from sodium hydrogen carbonate, sodium carbonate, disodium hydrogen phosphate, sodium phosphate, potassium carbonate, dipotassium hydrogen phosphate, potassium phosphate, potassium hydrogen carbonate, potassium hydroxide, sodium carbonate hydrate, sodium acetate, sodium tripolyphosphate, sodium phosphate dodecahydrate, diammonium hydrogen phosphate, sodium silicate, sodium trisilicate, sodium polyphosphate, sodium, potassium pyrophosphate, and any combination thereof.

In another embodiment, the said sulfonamide herbicide free acid is selected from nicosulfuron, tribenuron, metsulfuron, bensulfuron, penoxsulam, rimsulfuron, sulfometuron, thifensulfuon, mesosulfuron, pyrazosulfuron, chlorsulfuron, tritosulfuron, azimsulfuron, amidosulfuron, ethametsulfuron, chlorimuron, diclosulam, florasulam, flumetsulam, metosulam, and any combination thereof.

In another embodiment, the weight ratio of the said solid base to the sulfonamide herbicide free acid in the said agrochemical composition is from 1:90 to 90:1; the said solid base is present in an amount of at least 1% of the total weight of the agrochemical composition.

In the second aspect, the present invention provides a method of controlling field weeds, which comprises the application of the agrochemical composition mentioned in the first aspect of the present invention.

In the third aspect, the present invention provides a method of reducing and/or removing residues of the agrochemical composition comprising dicamba or its salt and a sulfonamide herbicide free acid in an application tank (e.g. spray tank). The method comprises providing the agrochemical composition mentioned in the first aspect of the present invention and applying the said agrochemical composition with an application tank (e.g. spray tank).

In the fourth aspect, the present invention provides a method of preparing an agrochemical composition which comprises the mixing of a solid base with dicamba or its salt and a sulfonamide herbicide free acid. For example, to prepare the agrochemical composition mentioned in the first aspect above through the said method.

In the fifth aspect, the present invention also provides a solid base for the use of reducing agrochemical composition residues in an application tank. The said agrochemical composition comprises dicamba or its salt and a sulfonamide herbicide free acid.

Compared to similar agrochemical compositions in the art, the agrochemical composition of the present invention, comprising a solid base, dicamba or its salt, and a sulfonamide herbicide free acid, can significantly reduce the residues of herbicidal active ingredients in an application tank (e.g. spray tank). Thus the said application tank does not require complicated and time-consuming treatment before using it for subsequent application of other agrochemical substances. This lowers or eradicates the adverse effect on the target of subsequent application.

DETAILED DESCRIPTION OF SPECIFIC EMBODIMENTS

Sulfonamide herbicides are a class of compounds of high herbicidal activity with sulfonylurea or triazolopyrimidine ascore structure. Suitable examples of sulfonamide herbicides include but not limited to nicosulfuron, tribenuron, metsulfuron, bensulfuron, penoxsulam, rimsulfuron, sulfometuron, thifensulfuon, mesosulfuron, pyrazosulfuron, chlorsulfuron, tritosulfuron, azimsulfuron, amidosulfuron, ethametsulfuron, chlorimuron, diclosulam, florasulam, flumetsulam and metosulam.

Compared with other conventional herbicides, sulfonamide herbicides have a significantly high herbicidal activity. However, the cost of sulfonamide herbicides is relatively high. In addition, the effect of a sulfonamide herbicide on controlling monocotyledonous weeds is better than that on dicotyledonous weeds. Therefore, agrochemical compositions comprising the combined use of a sulfonamide herbicide and other herbicides are known in the art.

It is desirable to clean out the spray equipment before the equipment is subsequently used to treat crops which are sensitive to the sulfonamide herbicide used in the previous application. Adequate cleanout may require a rinsing procedure that is time-consuming and results in wastewater disposal problem. Furthermore, cleanout can be affected if the spray equipment contains organic deposits remaining from previous crop protection chemical applications or from other chemicals tank-mixed with the sulfonamide herbicide. In respect of the abovementioned herbicidal mixtures of dicamba and sulfonamide, the problem of difficult spray tank cleanout is exacerbated by the increased amount of sulfonamide in the mixture of dicamba or its salt and sulfonamide. This is because the tank mixes of the mixture of dicamba or its salt and sulfonamide are primarily suspensions or emulsions. Suspended sulfonamide particles can accumulate on tank walls, in tubing, or be retained by organic deposits that may be present inside the tank. If a later tank mix transfers sulfonamide into solution or suspension, sensitive crops can be damaged.

This problem can be avoided by adding a solid base into the composition comprising dicamba or its salt and a sulfonamide free acid. Therefore, under general usage, only a few or even no sulfonamide particles accumulating on the interior surface of the tank or embedding in the organic deposit which may be formed on the surface.

Therefore, the present invention, in an embodiment, provides an agrochemical composition for controlling field weeds, which comprises at least one sulfonamide free acid herbicidal active ingredient, dicamba or its salt, and at least one solid base, optionally with at least one of the following ingredients as required: wetting agents, dispersing agents and diluents.

The said solid bases include those having cations derived from alkali metals or ammonium, and counterions selected from carbonate, phosphate, oxide, hydroxide, acetate and silicate anions, including dimeric, trimeric and polymeric forms thereof such as pyrophosphate, tripolyphosphate, polyphosphate and trisilicate, etc. Examples of solid bases include but not limited to the anhydrous and hydrated forms of sodium acetate (NaOAc), sodium phosphate ($Na_3PO_4$), disodium hydrogen phosphate ($Na_2HPO_4$), potassium phosphate ($K_3PO_4$), dipotassium hydrogen phosphate ($K_2HPO_4$), diammonium hydrogen phosphate (($NH_4)_2HPO_4$), sodium carbonate ($Na_2CO_3$), sodium hydrogen carbonate ($NaHCO_3$), potassium carbonate ($K_2CO_3$), potassium hydrogen carbonate ($KHCO_3$), lithium oxide ($Li_2O$), lithium hydroxide (LiOH), lithium carbonate ($Li_2CO_3$), sodium hydroxide (NaOH), lithium phosphate ($Li_3PO_4$), lithium silicate ($Li_2SiO_3$), lithium orthosilicate ($Li_4SiO_4$), potassium hydroxide (KOH), sodium silicate ($Na_2SiO_3$), sodium orthosilicate ($Na_4SiO_4$), potassium pyrophosphate ($K_4P_2O_7$), sodium trimetaphosphate (($NaPO_3)_3$), sodium hexametaphosphate (($NaPO_3)_6$), sodium polyphosphate (($NaPO_3)_n$), sodium pyrophosphate ($Na_4P_2O_7$), sodium tripolyphosphate ($Na_5P_3O_{10}$) and sodium trisilicate ($Na_2Si_3O_7$).

It has been surprisingly found that bases containing cations of alkali metals like sodium or potassium have excellent performance in the examples of the present invention. Therefore, it is preferable to choose bases containing cations of alkali metals like sodium ($Na^+$) and potassium ($K^+$), more preferably sodium. In addition, in consideration of cost, efficiency and convenience etc., it is more preferable to choose bases containing counterions selected from acetate ($OAc^-$), hydrogen carbonate ($HCO_3^-$), carbonate ($CO_3^{2-}$), hydrogen phosphate ($HPO_4^{2-}$) and phosphate ($PO_4^{3-}$). According to the result of the examples of the present invention, the inventor has also found that solid bases in the forms of carbonates and phosphates demonstrate excellent performance. Thus, carbonates and phosphates are more preferable. Preferred bases include sodium acetate, sodium carbonate, disodium hydrogen phosphate, sodium phosphate, potassium hydrogen carbonate, potassium carbonate, dipotassium hydrogen phosphate and potassium phosphate. The abovementioned bases include hydrated forms thereof, such as sodium carbonate monohydrate, disodium hydrogen phosphate hexahydrate, sodium phosphate dodecahydrate, potassium carbonate sesquihydrate, dipotassium hydrogen phosphate trihydrate and potassium phosphate octahydrate. According to the efficacy data from the abovementioned examples, more preferred are sodium carbonate, sodium phosphate, potassium carbonate and potassium phosphate, including hydrated forms thereof. The most preferable base is sodium carbonate, including hydrated forms thereof.

Addition of sufficient amount of a solid base into a composition comprising a sulfonamide free acid active ingredient and dicamba or its salt can enhance the solubility of the sulfonamide free acid active ingredient in water, resulting in a clear aqueous spray of herbicidal mixture comprising a sulfonamide free acid and dicamba, which in turn leads to a decrease in the amount of sulfonamide residues in the spray tank. The amount of the solid base required is based on the concentration of the sulfonamide free acid active ingredient. The weight ratio of the solid base to the sulfonamide free acid active ingredient is from 1:90 to 90:1. The solid base is present in an amount of at least 1% of the total weight of the agrochemical composition comprising the sulfonamide free acid active ingredient.

Wetting agents in the agrochemical composition of the present invention include but not limited to sodium alkyl sulfosuccinate, laurates, alkyl sulfate and phosphate esters, acetylenic diols, ethoxyfluorinated alcohols, ethoxylated silicones, alkyl phenol ethoxylates, benzene sulfonates, alkyl-substituted benzene sulfonates, alkyl á-olefin sulfonates, naphthalene sulfonates, alkyl-substituted naphthalene sulfonates, condensates of naphthalene sulfonates and alkyl-substituted naphthalene sulfonates with formaldehyde, and alcohol ethoxylates. Of note are compositions comprising up to 10% by weight on a water-free basis of the wetting agent.

Dispersing agents include but not limited to sodium, calcium and ammonium salts of lignosulfonic acid (optionally polyethoxylated); sodium and ammonium salts of maleic anhydride copolymers; sodium salts of condensed phenolsulfonic acid; and naphthalene sulfonate-formaldehyde condensates. Of note are compositions comprising up to 10% by weight on a water-free basis of the dispersing agent. Sodium lignosulfonate is particularly useful for the method and composition of the present invention.

Diluents may be water-soluble or -insoluble. Soluble diluents can be salts or saccharides that can dissolve quickly in water. Examples include but not limited to sodium dihydrogen phosphate, sodium, potassium, magnesium and zinc sulfates, sodium and potassium chlorides, sorbitol, sodium benzoate, lactose, and sucrose. Insoluble diluents include but not limited to clay, synthetic and diatomaceous silicas, calcium and magnesium silicates, titanium, aluminium, calcium and zinc oxides, calcium and magnesium carbonates, sodium sulfate, potassium sulfate, calcium and barium sulfates, and charcoal. Preferred are soluble diluents.

Apart from dicamba, at least one sulfonamide free acid active ingredient, at least one solid base, and optionally diluents, the agrochemical composition may also include stabilizers, adjuvant and coloring agents as appropriate.

The agrochemical composition of embodiments of the present invention can be in the form of wettable powder and water-soluble powder, etc, but more preferably in the form of water-soluble granule. Similarly, the dry formulations of the present invention can be in the form of aggregate, matrix or integrity, like block, granule, tablet, stick, film, and thin slice, etc. The dry formulations of the present invention are preferably to be embedded in soluble matrix or integrity. One skilled in the art has also realized that the present invention shall further include packing the fast-soluble dry formulations into soluble packages such as bags, pouches, sachets and capsules etc.

In addition, an embodiment of the present invention relates to a method of preparing a water-soluble granule (SG) comprising dicamba or its salt, at least one sulfonamide free acid active ingredient and at least one solid base for controlling field weeds. The method comprises the following steps:
(1) Preparing a mixture in powder form, which comprises dicamba, at least one sulfonamide free acid active ingredient, and at least one solid base;
(2) Adding water to the mixture;
(3) Extruding the wet mixture through a die to obtain granules;
(4) Drying the granules.

The present invention also provides an embodiment relating to administration method of a water-soluble granule, comprising:
(1) Preparing a water-soluble granule comprising a mixture of dicamba or its salt, at least one sulfonamide free acid active ingredient and at least one solid base;
(2) Mixing the water-soluble granule with water to obtain a clear diluted solution;
(3) Applying the agrochemical/water mixture.

The present invention also involves an embodiment relating to the preparation of an agrochemical/water mixture by using the said method.

The said dry formulations can be applied with the methods well known in the art. These methods include coating, spraying, dip, soaking, injection, and irrigation, etc.

The agrochemical composition of embodiments of the present invention is usually applied after dilution with water. One skilled in the art shall find that, while diluting by water, the dilution factor of the agrochemical composition varies according to types of agrochemical composition, types of harmful organisms to be controlled, types of crops to be treated, types of bacteria to be reduced, types of weeds to be controlled, duration of treatment and methods of application etc. However, the range is usually within 20 to 10,000 times.

In the present invention, unless otherwise specified, all percentages (expressing ratio or content) are by weight.

EXAMPLES

Example 1

40% Dicamba+6% Nicosulfuron SG (Water-Soluble Granule)

| | |
|---|---|
| Dicamba | 40% |
| Nicosulfuron | 6% |
| Supralate ® (sodium lauryl sulfate, Witco Inc., Greenwich) | 0.5% |
| Reax ® 88B (sodium lignosulfonate, Westvaco Corp) | 5% |
| Sodium carbonate ($Na_2CO_3$) | 1% |
| Potassium sulfate ($K_2SO_4$) | 47.5% |

The abovementioned substances are well-mixed and milled with suitable amount of water to form granules, and the said formulations is obtained after drying of the granules.

Comparative Example A

40% Dicamba+6% Nicosulfuron SG

| | |
|---|---|
| Dicamba | 40% |
| Nicosulfuron | 6% |
| Supralate ® (sodium lauryl sulfate, Witco Inc., Greenwich) | 0.5% |
| Reax ® 88B (sodium lignosulfonate, Westvaco Corp) | 5% |
| Potassium sulfate (K$_2$SO$_4$) | 48.5% |

The abovementioned substances are well-mixed and milled with suitable amount of water to form granules, and the said formulations is obtained after drying of the granules.

Example 2

1% Dicamba+1% Nicosulfuron SP (Water-Soluble Powder)

| | |
|---|---|
| Dicamba | 1% |
| Nicosulfuron | 1% |
| Supralate ® (sodium lauryl sulfate, Witco Inc., Greenwich) | 0.5% |
| Reax ® 88B (sodium lignosulfonate, Westvaco Corp) | 2.5% |
| Sodium carbonate (Na$_2$CO$_3$) | 1% |
| Sodium acetate (NaOAc) | 89% |

The active ingredients are thoroughly mixed with the adjuvant, and milled in a suitable mill to form the water-soluble powder.

Comparative Example B

1% Dicamba+1% Nicosulfuron SP

| | |
|---|---|
| Dicamba | 1% |
| Nicosulfuron | 1% |
| Supralate ® (sodium lauryl sulfate, Witco Inc., Greenwich) | 0.5% |
| Reax ® 88B (sodium lignosulfonate, Westvaco Corp) | 2.5% |
| Sucrose | 90% |

The active ingredients are thoroughly mixed with the adjuvant, and milled in a suitable mill to form the water-soluble powder.

Example 3

3.5% Dicamba+90% Nicosulfuron SP

| | |
|---|---|
| Dicamba | 3.5% |
| Nicosulfuron | 90% |
| Supralate ® (sodium lauryl sulfate, Witco Inc., Greenwich) | 0.5% |
| Reax ® 88B (sodium lignosulfonate, Westvaco Corp) | 5% |
| Sodium carbonate (Na$_2$CO$_3$) | 1% |

The active ingredients are thoroughly mixed with the adjuvant, and milled in a suitable mill to form the water-soluble powder.

Comparative Example C 3.5% Dicamba+90% Nicosulfuron SP

| | |
|---|---|
| Dicamba | 3.5% |
| Nicosulfuron | 90% |
| Supralate ® (sodium lauryl sulfate, Witco Inc., Greenwich) | 0.5% |
| Reax ® 88B (sodium lignosulfonate, Westvaco Corp) | 5% |
| Sucrose | 1% |

The active ingredients are thoroughly mixed with the adjuvant, and milled in a suitable mill to form the water-soluble powder.

Example 4

9% Dicamba+15% Nicosulfuron SG

| | |
|---|---|
| Dicamba | 9% |
| Nicosulfuron | 15% |
| Supralate ® (sodium lauryl sulfate, Witco Inc., Greenwich) | 0.5% |
| Reax ® 88B (sodium lignosulfonate, Westvaco Corp) | 5% |
| Sodium carbonate monohydrate (Na$_2$CO$_3$•H$_2$O) | 20% |
| Lactose | 50.5% |

The abovementioned substances are well-mixed and milled with suitable amount of water to form granules, and the said formulations is obtained after drying of the granules.

Comparative Example D

9% Dicamba+15% Nicosulfuron SG

| | |
|---|---|
| Dicamba | 9% |
| Nicosulfuron | 15% |
| Supralate ® (sodium lauryl sulfate, Witco Inc., Greenwich) | 0.5% |
| Reax ® 88B (sodium lignosulfonate, Westvaco Corp) | 5% |
| Lactose | 70.5% |

The abovementioned substances are well-mixed and milled with suitable amount of water to form granules, and the said formulations is obtained after drying of the granules.

Example 5

60% Dicamba+15% Nicosulfuron SP

| | |
|---|---|
| Dicamba | 60% |
| Nicosulfuron | 15% |
| Supralate ® (sodium lauryl sulfate, Witco Inc., Greenwich) | 0.5% |
| Reax ® 88B (sodium lignosulfonate, Westvaco Corp) | 5% |
| Sodium phosphate (Na$_3$PO$_4$) | 19.5% |

The active ingredients are thoroughly mixed with the adjuvant, and milled in a suitable mill to form the water-soluble powder.

Comparative Example E

60% Dicamba+15% Nicosulfuron SP

| | |
|---|---|
| Dicamba | 60% |
| Nicosulfuron | 15% |
| Supralate ® (sodium lauryl sulfate, Witco Inc., Greenwich) | 0.5% |
| Reax ® 88B (sodium lignosulfonate, Westvaco Corp) | 5% |
| Lactose | 19.5% |

The active ingredients are thoroughly mixed with the adjuvant, and milled in a suitable mill to form the water-soluble powder.

Example 6

30% Dicamba+10% Pyrazosulfuron SG

| | |
|---|---|
| Dicamba | 30% |
| Pyrazosulfuron | 10% |
| Supralate ® (sodium lauryl sulfate, Witco Inc., Greenwich) | 0.5% |
| Reax ® 88B (sodium lignosulfonate, Westvaco Corp) | 5% |
| Potassium carbonate ($K_2CO_3$) | 10% |
| Lactose | 44.5% |

The abovementioned substances are well mixed and milled with suitable amount of water to form granules, and the said formulation is obtained after drying of the granules.

Comparative Example F

30% Dicamba+10% Pyrazosulfuron SG

| | |
|---|---|
| Dicamba | 30% |
| Pyrazosulfuron | 10% |
| Supralate ® (sodium lauryl sulfate, Witco Inc., Greenwich) | 0.5% |
| Reax ® 88B (sodium lignosulfonate, Westvaco Corp) | 5% |
| Lactose | 54.5% |

The abovementioned substances are well-mixed and milled with suitable amount of water to form granules, and the said formulation is obtained after drying of the granules.

Example 7

48% Dicamba+2% Tribenuron SG

| | |
|---|---|
| Dicamba | 48% |
| Tribenuron | 2% |
| Supralate ® (sodium lauryl sulfate, Witco Inc., Greenwich) | 0.5% |
| Reax ® 88B (sodium lignosulfonate, Westvaco Corp) | 5% |
| Potassium hydrogen carbonate ($KHCO_3$) | 40% |
| Sucrose | 4.5% |

The abovementioned substances are well-mixed and milled with suitable amount of water to form granules, and the said formulation is obtained after drying of the granules.

Comparative Example G

48% Dicamba+2% Tribenuron SG

| | |
|---|---|
| Dicamba | 48% |
| Tribenuron | 2% |
| Supralate ® (sodium lauryl sulfate, Witco Inc., Greenwich) | 0.5% |
| Reax ® 88B (sodium lignosulfonate, Westvaco Corp) | 5% |
| Sucrose | 44.5% |

The abovementioned substances are well-mixed and milled with suitable amount of water to form granules, and the said formulation is obtained after drying of the granules.

Example 8

4% Dicamba+40% Ethametsulfuron SG

| | |
|---|---|
| Dicamba | 4% |
| Ethametsulfuron | 40% |
| Supralate ® (sodium lauryl sulfate, Witco Inc., Greenwich) | 0.5% |
| Reax ® 88B (sodium lignosulfonate, Westvaco Corp) | 5% |
| Sodium hydrogen carbonate ($NaHCO_3$) | 2% |
| Lactose | 48.5% |

The abovementioned substances are well-mixed and milled with suitable amount of water to form granules, and the said formulation is obtained after drying of the granules.

Comparative Example H

4% Dicamba+40% Ethametsulfuron SG

| | |
|---|---|
| Dicamba | 4% |
| Ethametsulfuron | 40% |
| Supralate ® (sodium lauryl sulfate, Witco Inc., Greenwich) | 0.5% |
| Reax ® 88B (sodium lignosulfonate, Westvaco Corp) | 5% |
| Lactose | 50.5% |

The abovementioned substances are well-mixed and milled with suitable amount of water to form granules, and the said formulation is obtained after drying of the granules.

Example 9

49% Dicamba+1% Florasulam SG

| | |
|---|---|
| Dicamba | 49% |
| Florasulam | 1% |
| Supralate ® (sodium lauryl sulfate, Witco Inc., Greenwich) | 0.5% |
| Reax ® 88B (sodium lignosulfonate, Westvaco Corp) | 5% |
| Disodium hydrogen phosphate ($Na_2HPO_4$) | 10% |
| Lactose | 34.5% |

The abovementioned substances are well-mixed and milled with suitable amount of water to form granules, and the said formulation is obtained after drying of the granules.

Comparative Example I

49% Dicamba+1% Florasulam SG

| | |
|---|---|
| Dicamba | 49% |
| Florasulam | 1% |
| Supralate ® (sodium lauryl sulfate, Witco Inc., Greenwich) | 0.5% |
| Reax ® 88B (sodium lignosulfonate, Westvaco Corp) | 5% |
| Lactose | 44.5% |

The abovementioned substances are well-mixed and milled with suitable amount of water to form granules, and the said formulation is obtained after drying of the granules.

Example 10

5% Dicamba+50% Diclosulam SG

| | |
|---|---|
| Dicamba | 5% |
| Diclosulam | 50% |
| Supralate ® (sodium lauryl sulfate, Witco Inc., Greenwich) | 0.5% |
| Reax ® 88B (sodium lignosulfonate, Westvaco Corp) | 5% |
| Potassium hydroxide | 1% |
| Lactose | 38.5% |

The abovementioned substances are well-mixed and milled with suitable amount of water to form granules, and the said formulation is obtained after drying of the granules.

Comparative Example J

5% Dicamba+50% Diclosulam SG

| | |
|---|---|
| Dicamba | 5% |
| Diclosulam | 50% |
| Supralate ® (sodium lauryl sulfate, Witco Inc., Greenwich) | 0.5% |
| Reax ® 88B (sodium lignosulfonate, Westvaco Corp) | 5% |
| Lactose | 39.5% |

The abovementioned substances are well-mixed and milled with suitable amount of water to form granules, and the said formulation is obtained after drying of the granules.

Example 11

18% Dicamba+1% Metsulfuron SG

| | |
|---|---|
| Dicamba | 18% |
| Metsulfuron | 1% |
| Supralate ® (sodium lauryl sulfate, Witco Inc., Greenwich) | 0.5% |
| Reax ® 88B (sodium lignosulfonate, Westvaco Corp) | 5% |
| Potassium hydrogen carbonate ($KHCO_3$) | 50% |
| Lactose | 25.5% |

The abovementioned substances are well-mixed and milled with suitable amount of water to form granules, and the said formulation is obtained after drying of the granules.

Comparative Example K

18% Dicamba+1% Metsulfuron SG

| | |
|---|---|
| Dicamba | 18% |
| Metsulfuron | 1% |
| Supralate ® (sodium lauryl sulfate, Witco Inc., Greenwich) | 0.5% |
| Reax ® 88B (sodium lignosulfonate, Westvaco Corp) | 5% |
| Lactose | 75.5% |

The abovementioned substances are well-mixed and milled with suitable amount of water to form granules, and the said formulation is obtained after drying of the granules.

Example 12

10% Dicamba+50% Bensulfuron SG

| | |
|---|---|
| Dicamba | 10% |
| Bensulfuron | 50% |
| Supralate ® (sodium lauryl sulfate, Witco Inc., Greenwich) | 0.5% |
| Reax ® 88B (sodium lignosulfonate, Westvaco Corp) | 5% |
| Potassium phosphate ($K_3PO_4$) | 1% |
| Sucrose | 33.5% |

The abovementioned substances are well-mixed and milled with suitable amount of water to form granules, and the said formulation is obtained after drying of the granules.

Comparative Example L

10% Dicamba+50% Bensulfuron SG

| | |
|---|---|
| Dicamba | 10% |
| Bensulfuron | 50% |
| Supralate ® (sodium lauryl sulfate, Witco Inc., Greenwich) | 0.5% |
| Reax ® 88B (sodium lignosulfonate, Westvaco Corp) | 5% |
| Sucrose | 34.5% |

The abovementioned substances are well-mixed and milled with suitable amount of water to form granules, and the said formulation is obtained after drying of the granules.

Example 13

60% Dicamba+10% Penoxsulam SG

| | |
|---|---|
| Dicamba | 60% |
| Penoxsulam | 10% |
| Supralate ® (sodium lauryl sulfate, Witco Inc., Greenwich) | 0.5% |
| Reax ® 88B (sodium lignosulfonate, Westvaco Corp) | 5% |
| Dipotassium hydrogen phosphate ($K_2HPO_4$) | 1% |
| Sucrose | 23.5% |

The abovementioned substances are well-mixed and milled with suitable amount of water to form granules, and the said formulation is obtained after drying of the granules.

Comparative Example M

60% Dicamba+10% Penoxsulam SG

| | |
|---|---|
| Dicamba | 60% |
| Penoxsulam | 10% |
| Supralate ® (sodium lauryl sulfate, Witco Inc., Greenwich) | 0.5% |
| Reax ® 88B (sodium lignosulfonate, Westvaco Corp) | 5% |
| Sucrose | 24.5% |

The abovementioned substances are well-mixed and milled with suitable amount of water to form granules, and the said formulation is obtained after drying of the granules.

Example 14

40% Dicamba+5% Rimsulfuron SG

| | |
|---|---|
| Dicamba | 40% |
| Rimsulfuron | 5% |
| Supralate ® (sodium lauryl sulfate, Witco Inc., Greenwich) | 0.5% |
| Reax ® 88B (sodium lignosulfonate, Westvaco Corp) | 4.5% |
| Sodium phosphate dodecahydrate ($Na_3PO_4 \cdot 12H_2O$) | 50% |

The abovementioned substances are well-mixed and milled with suitable amount of water to form granules, and the said formulation is obtained after drying of the granules.

Comparative Example N

40% Dicamba+5% Rimsulfuron SG

| | |
|---|---|
| Dicamba | 40% |
| Rimsulfuron | 5% |
| Supralate ® (sodium lauryl sulfate, Witco Inc., Greenwich) | 0.5% |
| Reax ® 88B (sodium lignosulfonate, Westvaco Corp) | 4.5% |
| Lactose | 50% |

The abovementioned substances are well-mixed and milled with suitable amount of water to form granules, and the said formulation is obtained after drying of the granules.

Example 15

60% Dicamba+5% Sulfometuron SG

| | |
|---|---|
| Dicamba | 60% |
| Sulfometuron | 5% |
| Supralate ® (sodium lauryl sulfate, Witco Inc., Greenwich) | 0.5% |
| Reax ® 88B (sodium lignosulfonate, Westvaco Corp) | 4.5% |
| Potassium pyrophosphate ($K_4P_2O_7$) | 1% |
| Lactose | 29% |

The abovementioned substances are well-mixed and milled with suitable amount of water to form granules, and the said formulation is obtained after drying of the granules.

Comparative Example O

60% Dicamba+5% Sulfometuron SG

| | |
|---|---|
| Dicamba | 60% |
| Sulfometuron | 5% |
| Supralate ® (sodium lauryl sulfate, Witco Inc., Greenwich) | 0.5% |
| Reax ® 88B (sodium lignosulfonate, Westvaco Corp) | 4.5% |
| Lactose | 30% |

The abovementioned substances are well-mixed and milled with suitable amount of water to form granules, and the said formulation is obtained after drying of the granules.

Example 16

40% Dicamba+5% Thifensulfuon SG

| | |
|---|---|
| Dicamba | 40% |
| Thifensulfuon | 5% |
| Supralate ® (sodium lauryl sulfate, Witco Inc., Greenwich) | 0.5% |
| Reax ® 88B (sodium lignosulfonate, Westvaco Corp) | 4.5% |
| Diammonium hydrogen phosphate (($NH_4)_2HPO_4$) | 25% |
| Lactose | 25% |

The abovementioned substances are well-mixed and milled with suitable amount of water to form granules, and the said formulation is obtained after drying of the granules.

Comparative Example P

40% Dicamba+5% Thifensulfuon SG

| | |
|---|---|
| Dicamba | 40% |
| Thifensulfuon | 5% |
| Supralate ® (sodium lauryl sulfate, Witco Inc., Greenwich) | 0.5% |
| Reax ® 88B (sodium lignosulfonate, Westvaco Corp) | 4.5% |
| Lactose | 50% |

The abovementioned substances are well-mixed and milled with suitable amount of water to form granules, and the said formulation is obtained after drying of the granules.

Example 17

20% Dicamba+10% Mesosulfuron SG

| | |
|---|---|
| Dicamba | 20% |
| Mesosulfuron | 10% |
| Supralate ® (sodium lauryl sulfate, Witco Inc., Greenwich) | 0.5% |
| Reax ® 88B (sodium lignosulfonate, Westvaco Corp) | 4.5% |
| Sodium silicate ($Na_2SiO_3$) | 10% |
| Sucrose | 55% |

The abovementioned substances are well-mixed and milled with suitable amount of water to form granules, and the said formulation is obtained after drying of the granules.

Comparative Example Q

20% Dicamba+10% Mesosulfuron SG

| | |
|---|---|
| Dicamba | 20% |
| Mesosulfuron | 10% |
| Supralate ® (sodium lauryl sulfate, Witco Inc., Greenwich) | 0.5% |
| Reax ® 88B (sodium lignosulfonate, Westvaco Corp) | 4.5% |
| Sucrose | 65% |

The abovementioned substances are well-mixed and milled with suitable amount of water to form granules, and the said formulation is obtained after drying of the granules.

Example 18

29.2% Dicamba+1.5% Amidosulfuron SG

| | |
|---|---|
| Dicamba | 29.2% |
| Amidosulfuron | 1.5% |
| Supralate ® (sodium lauryl sulfate, Witco Inc., Greenwich) | 0.5% |
| Reax ® 88B (sodium lignosulfonate, Westvaco Corp) | 4.5% |
| Sodium tripolyphosphate ($Na_5P_3O_{10}$) | 3% |
| Lactose | 61.3% |

The abovementioned substances are well-mixed and milled with suitable amount of water to form granules, and the said formulation is obtained after drying of the granules.

Comparative Example R

29.2% Dicamba+1.5% Amidosulfuron SG

| | |
|---|---|
| Dicamba | 29.2% |
| Amidosulfuron | 1.5% |
| Supralate ® (sodium lauryl sulfate, Witco Inc., Greenwich) | 0.5% |
| Reax ® 88B (sodium lignosulfonate, Westvaco Corp) | 4.5% |
| Lactose | 64.3% |

The abovementioned substances are well-mixed and milled with suitable amount of water to form granules, and the said formulation is obtained after drying of the granules.

Example 19

40% Dicamba+20% Azimsulfuron SG

| | |
|---|---|
| Dicamba | 40% |
| Azimsulfuron | 20% |
| Supralate ® (sodium lauryl sulfate, Witco Inc., Greenwich) | 0.5% |
| Reax ® 88B (sodium lignosulfonate, Westvaco Corp) | 4.5% |
| Sodium trisilicate ($Na_2Si_3O_7$) | 5% |
| Sucrose | 30% |

The abovementioned substances are well-mixed and milled with suitable amount of water to form granules, and the said formulation is obtained after drying of the granules.

Comparative Example S

40% Dicamba+20% Azimsulfuron SG

| | |
|---|---|
| Dicamba | 40% |
| Azimsulfuron | 20% |
| Supralate ® (sodium lauryl sulfate, Witco Inc., Greenwich) | 0.5% |
| Reax ® 88B (sodium lignosulfonate, Westvaco Corp) | 4.5% |
| Sucrose | 35% |

The abovementioned substances are well-mixed and milled with suitable amount of water to form granules, and the said formulation is obtained after drying of the granules.

Example 20

30% Dicamba+30% Chlorimuron SG

| | |
|---|---|
| Dicamba | 30% |
| Chlorimuron | 30% |
| Supralate ® (sodium lauryl sulfate, Witco Inc., Greenwich) | 0.5% |
| Reax ® 88B (sodium lignosulfonate, Westvaco Corp) | 4.5% |
| Sodium polyphosphate ($(NaPO_3)_n$) | 20% |
| Lactose | 15% |

The abovementioned substances are well-mixed and milled with suitable amount of water to form granules, and the said formulation is obtained after drying of the granules.

Comparative Example T

30% Dicamba+30% Chlorimuron SG

| | |
|---|---|
| Dicamba | 30% |
| Chlorimuron | 30% |
| Supralate ® (sodium lauryl sulfate, Witco Inc., Greenwich) | 0.5% |
| Reax ® 88B (sodium lignosulfonate, Westvaco Corp) | 4.5% |
| Lactose | 35% |

The abovementioned substances are well-mixed and milled with suitable amount of water to form granules, and the said formulation is obtained after drying of the granules.

Example 21

20% Dicamba+60% Tritosulfuron SG

| | |
|---|---|
| Dicamba | 20% |
| Tritosulfuron | 60% |
| Supralate ® (sodium lauryl sulfate, Witco Inc., Greenwich) | 0.5% |
| Reax ® 88B (sodium lignosulfonate, Westvaco Corp) | 4.5% |
| Sodium hexametaphosphate ($(NaPO_3)_6$) | 15% |

The abovementioned substances are well-mixed and milled with suitable amount of water to form granules, and the said formulation is obtained after drying of the granules.

Comparative Example U

20% Dicamba+60% Tritosulfuron SG

| | |
|---|---|
| Dicamba | 20% |
| Tritosulfuron | 60% |
| Supralate ® (sodium lauryl sulfate, Witco Inc., Greenwich) | 0.5% |
| Reax ® 88B (sodium lignosulfonate, Westvaco Corp) | 4.5% |
| Lactose | 15% |

The abovementioned substances are well-mixed and milled with suitable amount of water to form granules, and the said formulation is obtained after drying of the granules.

Example 22

10% Dicamba+70% Chlorsulfuron SG

| | |
|---|---|
| Dicamba | 10% |
| Chlorsulfuron | 70% |
| Supralate ® (sodium lauryl sulfate, Witco Inc., Greenwich) | 0.5% |
| Reax ® 88B (sodium lignosulfonate, Westvaco Corp) | 4.5% |
| Sodium silicate (($Na_2SiO_3$)$_6$) | 15% |

The abovementioned substances are well-mixed and milled with suitable amount of water to form granules, and the said formulation is obtained after drying of the granules.

Comparative Example V

10% Dicamba+70% Chlorsulfuron SG

| | |
|---|---|
| Dicamba | 10% |
| Chlorsulfuron | 70% |
| Supralate ® (sodium lauryl sulfate, Witco Inc., Greenwich) | 0.5% |
| Reax ® 88B (sodium lignosulfonate, Westvaco Corp) | 4.5% |
| Sucrose | 15% |

The abovementioned substances are well-mixed and milled with suitable amount of water to form granules, and the said formulation is obtained after drying of the granules.

Laboratory Cleanout Test Procedure

The test is conducted on the diluted solutions obtained by dispersing the samples of Examples 1 to 22 and Comparative examples A to V in water. 1 g of the samples is added to tap water (300 mL) in a 400-mL beaker for magnetic stirring for 2 minutes. The resulting diluted solution is dispensed in three 100 mL aliquots to 4-oz (118-mL) polyethylene bottles. The bottles are capped, inverted twice and allowed to stand overnight. After standing overnight, each individual bottle is inverted twice and the liquid contents are then poured out. Tap water (10 mL) is added and the bottle is inverted until all sediments are re-suspended, whereupon the contents are poured out. Tap water (10 mL) is added and the bottle is inverted twice and then allowed to stand undisturbed for 10 minutes. The bottle is inverted twice more and the contents are poured out. Acetonitrile (10 mL) is added to the bottle to extract any remaining material. The acetonitrile solution is analyzed by a reversed-phase liquid chromatography with UV detector. The cleanout rate (the concentration of sulfonamide in acetonitrile solution) is reported in ppm in the following table. Lower cleanout ratings indicate more efficient cleanout when compared to higher ratings.

| Ex. | Sulfonamide ingredient | Amount of sulfonamide (%) | Base ingredient | Base (%) | Sulfonamide: Base | Cleanout rating (ppm sulfonamide) |
|---|---|---|---|---|---|---|
| 1 | Nicosulfuron | 6% | Sodium carbonate | 1% | 6:1 | 0 |
| 2 | Nicosulfuron | 1% | Sodium carbonate Sodium acetate | 90% | 1:90 | 0 |
| 3 | Nicosulfuron | 90% | Sodium carbonate | 1% | 90:1 | 50 |
| 4 | Nicosulfuron | 15% | Sodium carbonate monohyrdrate | 20% | 3:4 | 2 |
| 5 | Nicosulfuron | 15% | Sodium phosphate | 19.5% | 1:1.3 | 4 |
| 6 | Pyrazosulfuron | 10% | Potassium carbonate | 10% | 1:1 | 10 |
| 7 | Tribenuron | 2% | Potassium hydrogen carbonate | 40% | 1:20 | 5 |
| 8 | Ethametsulfuron | 40% | Sodium hydrogen carbonate | 2% | 20:1 | 6 |
| 9 | Florasulam | 1% | Disodium hydrogen phosphate | 10% | 1:10 | 15 |
| 10 | Diclosulam | 50% | Potassium hydroxide | 1% | 50:1 | 5 |
| 11 | Metsulfuron | 1% | Potassium hydrogen carbonate | 50% | 1:50 | 3 |
| 12 | Bensulfuron | 50% | Potassium phosphate | 1% | 50:1 | 25 |
| 13 | Penoxsulam | 10% | Dipotassium hydrogen phosphate | 1% | 10:1 | 20 |
| 14 | Rimsulfuron | 5% | Sodium phosphate dodecahydrate | 50% | 1:10 | 0 |
| 15 | Sulfometuron | 5% | Potassium pyrophosphate | 1% | 5:1 | 9 |

-continued

| Ex. | Sulfonamide ingredient | Amount of sulfonamide (%) | Base ingredient | Base (%) | Sulfonamide:Base | Cleanout rating (ppm sulfonamide) |
|---|---|---|---|---|---|---|
| 16 | Thifensulfuon | 5% | Diammonium hydrogen phosphate | 25% | 1:5 | 5 |
| 17 | Mesosulfuron | 10% | Sodium silicate | 10% | 1:1 | 7 |
| 18 | Amidosulfuron | 1.5% | Sodium tripolyphosphate | 3% | 1:2 | 1 |
| 19 | Azimsulfuron | 20% | Sodium trisilicate | 5% | 4:1 | 60 |
| 20 | Chlorimuron | 30% | Sodium polyphoshate | 20% | 3:2 | 46 |
| 21 | Tritosulfuron | 60% | Sodium hexametaphosphate | 15% | 4:1 | 30 |
| 22 | Chlorsulfuron | 70% | Sodium silicate | 15% | 4.7:1 | 25 |
| A | Nicosulfuron | 6% | nil | nil | nil | 1000 |
| B | Nicosulfuron | 1% | nil | nil | nil | 400 |
| C | Nicosulfuron | 90% | nil | nil | nil | 890,123 |
| D | Nicosulfuron | 15% | nil | nil | nil | 34,213 |
| E | Nicosulfuron | 15% | nil | nil | nil | 53,254 |
| F | Pyrazosulfuron | 10% | nil | nil | nil | 28,900 |
| G | Tribenuron | 2% | nil | nil | nil | 800 |
| H | Ethametsulfuron | 40% | nil | nil | nil | 320,180 |
| I | Tribenuron | 1% | nil | nil | nil | 500 |
| J | Tribenuron | 50% | nil | nil | nil | 432,980 |
| K | Metsulfuron | 1% | nil | nil | nil | 300 |
| L | Bensulfuron | 50% | nil | nil | nil | 443,650 |
| M | Penoxsulam | 10% | nil | nil | nil | 27,800 |
| N | Rimsulfuron | 5% | nil | nil | nil | 590 |
| O | Sulfometuron | 5% | nil | nil | nil | 850 |
| P | Thifensulfuon | 5% | nil | nil | nil | 740 |
| Q | Mesosulfuron | 10% | nil | nil | nil | 38,800 |
| R | Amidosulfuron | 1.5% | nil | nil | nil | 870 |
| S | Azimsulfuron | 20% | nil | nil | nil | 119,860 |
| T | Chlorimuron | 30% | nil | nil | nil | 250,000 |
| U | Tritosulfuron | 60% | nil | nil | nil | 430,245 |
| V | Chlorsulfuron | 70% | nil | nil | nil | 532,134 |

The cleanout rating data in the above table shows that adding a solid base into the herbicidal composition according to the present invention comprising dicamba and a sulfonamide free acid can significantly reduce the amount of sulfonamide residues in the bottle.

Bioassay Protocol:

The test is conducted on the diluted solutions obtained by dispersing 1 g of the samples of Examples 1 to 22 and Comparative examples A to V in water. The resulting diluted solution is dispensed in three 100-mL aliquots to 4-oz (118-mL) polyethylene bottles. The bottles are capped, inverted twice and allowed to stand overnight. After standing overnight, each individual bottle is inverted twice and the liquid contents are then poured out. Tap water (10 mL) is added and the bottle is inverted until all sediments are re-suspended, whereupon the contents are poured out. Tap water (10 mL) is added and the bottle is inverted twice and then allowed to stand undisturbed for 10 minutes. The bottle is inverted twice more and the contents are poured out. In the above cleanout procedure, acetonitrile (10 mL) is added to the bottle to extract any remaining material. The acetonitrile solution is analyzed by a reversed-phase liquid chromatography with UV detector. In this bioassay procedure, 1000 mL fresh water is added to the bottle. The final rinse solution is sprayed on the crops (sugar beet). The bioassay protocol employed shall determine the percent injury of the crop. Sugar beet seedlings (at the two-leaf stage) are grown in greenhouse (14 hours at 21° C. with light and 10 hours at 17° C. in the dark) and sprayed with the above final rinse solution. Three replicates, with four sugar beet plants/pot, are treated with each sample.

Plants are held in the greenhouse until they are evaluated 14 to 23 days after treatment. Injury of treated plants is assessed visually on a scale of 0 to 100 (0=no injury, 100=completely killed) compared to control plants. Injury ratings are based on the presence of various symptoms, including reduced biomass, stunting, inhibited development, chlorosis, necrosis, leaf spotting, and leaf puckering or deformation.

| Example | Injury level | Comparative example | Injury level |
|---|---|---|---|
| 1 | 0 | A | 20 |
| 2 | 0 | B | 20 |
| 3 | 5 | C | 100 |
| 4 | 0 | D | 60 |
| 5 | 0 | E | 60 |
| 6 | 0 | F | 60 |
| 7 | 0 | G | 30 |
| 8 | 0 | H | 100 |
| 9 | 0 | I | 20 |
| 10 | 0 | J | 100 |
| 11 | 0 | K | 10 |
| 12 | 0 | L | 100 |
| 13 | 0 | M | 50 |
| 14 | 0 | N | 20 |
| 15 | 0 | O | 30 |
| 16 | 0 | P | 20 |
| 17 | 0 | Q | 70 |
| 18 | 0 | R | 30 |
| 19 | 5 | S | 100 |

| Example | Injury level | Comparative example | Injury level |
|---|---|---|---|
| 20 | 5 | T | 100 |
| 21 | 5 | U | 100 |
| 22 | 5 | V | 100 |

The data in the above table shows that adding a solid base into the herbicidal composition according to the Examples 1 to 22 of the present invention comprising dicamba and a sulfonamide free acid can significantly reduce the sulfonamide residues in the spray tank. There is almost no injury shown on the sugar beet sprayed with the final rinse solution. The Comparative examples A to V show serious injuries on the sugar beet sprayed with the final rinse solution if the sulfonamide presents in an amount of more than 10% of the composition comprising dicamba and sulfonamide.

The invention claimed is:

1. An agrochemical composition comprising:
   dicamba or its salt, a sulfonamide herbicide free acid, a solid base and optionally an agriculturally acceptable carrier;
   wherein the sulfonamide herbicide free acid is nicosulfuron;
   wherein the weight ratio of the solid base to nicosulfuron is from 1:90 to 90:1;
   wherein the solid base is present in an amount of at least 1% of the total weight of the agrochemical composition; and
   wherein the presence of the solid base reduces the presence of nicosulfuron residue in an application tank and improves clean-out of nicosulfuron in the application tank relative to the agrochemical composition that does not include the solid base.

2. The agrochemical composition according to claim 1, wherein the agrochemical composition is in solid form.

3. The agrochemical composition according to claim 1, wherein the solid base is selected from one or more of the group consisting of sodium hydrogen carbonate, sodium carbonate, disodium hydrogen phosphate, sodium phosphate, potassium carbonate, dipotassium hydrogen phosphate, potassium phosphate, potassium hydrogen carbonate, potassium hydroxide, sodium carbonate hydrate, sodium acetate, sodium tripolyphosphate, sodium phosphate dodecahydrate, diammonium hydrogen phosphate, sodium silicate, sodium trisilicate, sodium polyphosphate, sodium hexametaphosphate and potassium pyrophosphate.

4. The agrochemical composition according to claim 3, wherein the solid base is selected from one or more of the group consisting of sodium acetate, sodium carbonate, disodium hydrogen phosphate, sodium phosphate, potassium hydrogen carbonate, potassium carbonate, dipotassium hydrogen phosphate and potassium phosphate.

5. A method of controlling field weeds, the method comprising applying to the field weeds the agrochemical composition according to claim 1.

6. A method according to claim 5 which further comprises applying the agrochemical composition with an application tank.

7. The agrochemical composition according to claim 2, wherein the agrochemical composition is in the form of wettable powder, water soluble powder or water soluble granule.

8. The agrochemical composition according to claim 7, wherein the agrochemical composition is in a form of a water soluble granule.

9. The agrochemical composition according to claim 4, wherein the solid base is selected from the group consisting of sodium carbonate, sodium phosphate, potassium carbonate and potassium phosphate.

10. The agrochemical composition according to claim 9, wherein the solid base is sodium carbonate.

11. The method according to claim 6, wherein the application tank is a spray tank.

12. A method of preparing an agrochemical composition, comprising the mixing of a solid base with dicamba or its salt and a nicosulfuron to establish a weight ratio of the solid base to nicosulfuron from 1:90 to 90:1 and the presence of the solid base in an amount of at least 1% of the total weight of the agrochemical composition, wherein the presence of the solid base reduces the presence of nicosulfuron residue in the application tank and improves clean-out of the nicosulfuron in the application tank relative to the agrochemical composition that is not prepared with the solid base.

* * * * *